US005582986A

United States Patent [19]
Monia et al.

[11] Patent Number: 5,582,986
[45] Date of Patent: * Dec. 10, 1996

[54] ANTISENSE OLIGONUCLEOTIDE INHIBITION OF THE RAS GENE

[75] Inventors: Brett P. Monia, Carlsbad; Susan M. Freier, San Diego; David J. Ecker, Leucadia, all of Calif.

[73] Assignee: Isis Pharmaceuticals, Inc., Carlsbad, Calif.

[*] Notice: The term of this patent shall not extend beyond the expiration date of Pat. No. 5,576,208.

[21] Appl. No.: 293,086

[22] Filed: Aug. 19, 1994

Related U.S. Application Data

[63] Continuation of Ser. No. 958,134, Oct. 5, 1992, abandoned, which is a continuation-in-part of Ser. No. 715,196, Jun. 14, 1991, abandoned.

[51] Int. Cl.$^6$ ............... C12Q 1/68; A61K 31/70; C07H 21/02; C07H 21/04
[52] U.S. Cl. ............... 435/6; 514/44; 536/24.3; 536/24.5
[58] Field of Search ............... 435/6; 536/23.1, 536/24.1, 24.3, 24.5; 514/44

[56] References Cited

U.S. PATENT DOCUMENTS

| | | | |
|---|---|---|---|
| 4,871,838 | 10/1989 | Bos et al. | 536/27 |
| 5,087,617 | 5/1992 | Smith | 514/44 |

FOREIGN PATENT DOCUMENTS

WO88/07544  10/1988  WIPO.

OTHER PUBLICATIONS

Uhlmann et al. (1990) Caert Rev. 90(4), 543–584.
Monia et al. (1992) J. Biol. Chem. vol 267(28):19954–19962.
Daaka et al. (1990) Oncogene Research vol. 5:267–275.
Bos (1988) Mutation Research vol. 195:255–271.
Feramisco et al., Transient reversion of ras oncogene-induced cell transformation by antibodies specific for amino acid 12 of ras protein, *Nature*, 314:639–642, 1985.
Holt et al., An Oligomer Complementary to c–myc mRNA Inhibits Proliferation of HL–60 Promyelocytic Cells and Induces Differentiation, *Mol. Cell Biol.*, 8, 963–973, 1988.
Anfossi et al., An Oligomer Complementary to c–myb–encoded mRNA inhibits proliferation of human myeloid leukemia cell lines, *Proc. Natl. Acad. Sci.*, 86, 3379–3383, 1989.

Wickstrom et al., Human promyelocytic leukemia HL–60 cell proliferation and c–myc protein expression are inhibited by an antisense pentadecadeoxynucleotide targeted against c–myc m RNA, *Proc. Nat. Acad. Sci.*, 85, 1028–1032, 1988.
Tidd et al., Evaluation of N–ra oncogene anti–sense, sense and nonsense sequence methylphosphonate oligonucleotide analogues, *Anti–Cancer Drug Design*, 3, 117–127, 1988.
Chang et al., Comparative inhibition of ras p21 protein synthesis with phosphorus–modified antisense oligonucleotides, *Anti–Cancer Drug Design*, 4:221–32, 1989.
Puglisi and Tinoco *Methods in Enzymol.* 1989, 180, 304–325, Absorbance Melting Curves of RNA.
Petersheim, M. and D. H. Turner, Base–Stacking and Base–Pairing Contributions to Helix Stability: Thermodynamics of Double–Helix Formation with CCGG, CCGGp, CCGGAp, ACCGGp, CCGGUp and ACCGGUp, *Biochemistry* 1983, 22, 256–263.
Borer, P. N., et al., Stability of Ribonucleic Acid Double Stranded Helices, *J. Mol. Biol.*, 1974, 86, 843–853.
Saison–Behmoaras et al., Short Modified Antisense Oligonucleotides Directed Against Ha–ras Point Mutation Induce Selective Cleavage of the mRNA and Inhibit T24 Cells Proliferation, (1991) *EMBO J.* 10:1111–1118.
Greenberg, M. E., in *Current Protocols in Molecular Biology*, K. Strahl, eds., John Wiley and Sons, NY.

*Primary Examiner*—George C. Elliott
*Attorney, Agent, or Firm*—Law Offices of Jane Massey Licata

[57] ABSTRACT

Compositions and methods are provided for the modulation of expression of the human ras gene in both the normal and activated forms. Oligonucleotides are provided which are specifically hybridizable with RNA or DNA deriving from the human ras gene, having nucleotide units sufficient in identity and number to effect such specific hybridization. Oligonucleotides or oligonucleotide analogs specifically hybridizable with a translation initiation site or with the codon-12 mutation of activated ras are provided. Such oligonucleotides and oligonucleotide analogs can be used for diagnostics as well as for research purposes. Methods are also disclosed for modulating ras gene expression in cells and tissues using the oligonucleotides or oligonucleotide analogs provided, and for specific modulation of expression of the activated ras gene. Methods for diagnosis, detection and treatment of conditions arising from the activation of the H-ras gene are also disclosed.

6 Claims, 13 Drawing Sheets ggcccugaggaggcgAUGacggaauauaagcugguggugggcgccgUcgguguggcaagagugcgcug

| OLIGO | LENGTH | TARGET | IC50 (uM) | SELECTIVITY |
|---|---|---|---|---|
| 2502 | 20 | AUG | 0.75 | NONE |
| 2503 | 20 | AUG | 0.05 | NONE |
| 2563 | 5 | POINT | NOT ACTIVE | --- |
| 2564 | 7 | POINT | NOT ACTIVE | --- |
| 2565 | 9 | POINT | NOT ACTIVE | --- |
| 2567 | 11 | POINT | NOT ACTIVE | --- |
| 2568 | 13 | POINT | NOT ACTIVE | --- |
| 2569 | 15 | POINT | NOT ACTIVE | --- |
| 2570 | 17 | POINT | 0.10 | 2-3x |
| 2571 | 19 | POINT | 0.25 | NONE |
| 2566 | 21 | POINT | 0.25 | NONE |
| 2560 | 23 | POINT | 0.75 | NONE |
| 2561 | 25 | POINT | 1.00 | NONE |

*Fig. 4a*

| OLIGO | LENGTH | TARGET |
|---|---|---|
| 2502 | 20 | AUG |
| 2503 | 20 | AUG |
| 2563 | 5 | CODON 12 |
| 2564 | 7 | CODON 12 |
| 2565 | 9 | CODON 12 |
| 2567 | 11 | CODON 12 |
| 2568 | 13 | CODON 12 |
| 2569 | 15 | CODON 12 |
| 3426 | 16 | CODON 12 |
| 3427 | 16 | CODON 12 |
| 2570 | 17 | CODON 12 |
| 3428 | 18 | CODON 12 |
| 3429 | 18 | CODON 12 |
| 2571 | 19 | CODON 12 |
| 2566 | 21 | CODON 12 |
| 2560 | 23 | CODON 12 |
| 2561 | 25 | CODON 12 |
| 2907 | 17 | CODON 12 (wild type) | ggccccugaggagcgAUGacggaauauaagcugguggugguggccgcgUcggugugggccaagaguccgcug

G→ ctcgc t a c t gcct tatattc gggactcctcgc t a c tgcct gcagc
                                     ggcagcc
                                  cggcagcca
                              gcggcagccac
                            cgcggcagccaca
                        ccgcggcagccacac
                       ccgcggcagccacacc
                     cccgcggcagccacac
                   cccgcggcagccacacc
                  cccgcggcagccacaccc
                 acccgcggcagccacacc
                acccgcggcagccacaccc
               cacccgcggcagccacaccg
             ccacccgcggcagccacaccgt
           accacccgcggcagccacaccgtt cccgcgccgccacacc

*Fig. 5*

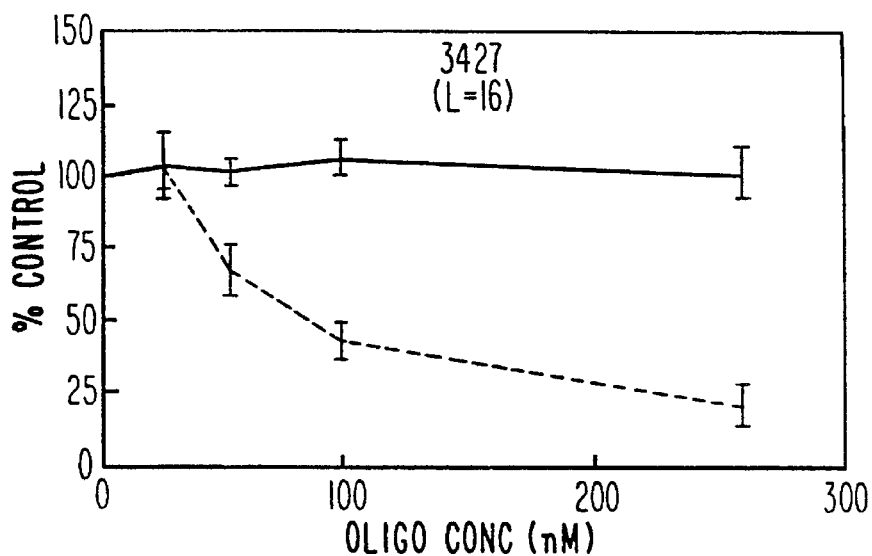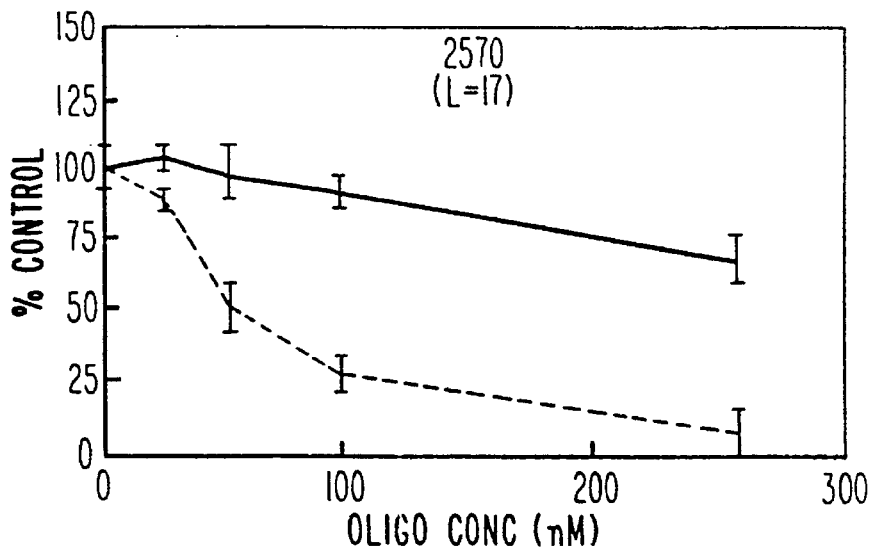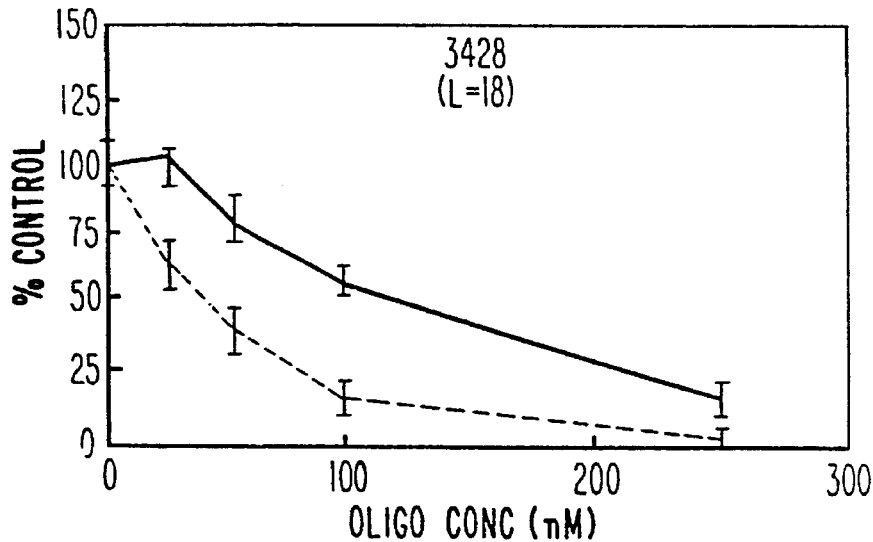

ANTISENSE OLIGONUCLEOTIDE INHIBITION OF THE RAS GENE

This is a continuation of application Ser. No. 07/958,134, filed Oct. 5, 1992, abandoned which is a continuation-in-part of U.S. patent application Ser. No. 715,196, filed Jun. 14, 1991, now abandoned and refiled as an FWC Ser. no. 08/032,752.

FIELD OF THE INVENTION

This invention relates to compositions and methods for the inhibition of expression of the ras gene, a naturally occurring gene which occasionally converts to an activated form which has been implicated in tumor formation. This invention is also directed to the specific inhibition of expression of the activated form of the ras gene. This invention is further directed to the detection of both normal and activated forms of the ras gene in cells and tissues, and can form the basis for research reagents and kits both for research and diagnosis. Furthermore, this invention is directed to treatment of such conditions as arise from activation of the ras gene.

BACKGROUND OF THE INVENTION

Alterations in the cellular genes which directly or indirectly control cell growth and differentiation are considered to be the main cause of cancer. There are some thirty families of genes, called oncogenes, which are implicated in human tumor formation. Members of one such family, the ras gene family, are frequently found to be mutated in human tumors. In their normal state, proteins produced by the ras genes are thought to be involved in normal cell growth and maturation. Mutation of the ras gene, causing an amino acid alteration at one of three critical positions in the protein product, results in conversion to a form which is implicated in tumor formation. A gene having such a mutation is said to be "activated." It is thought that such a point mutation leading to ras activation can be induced by carcinogene or other environmental factors. Over 90% of pancreatic adenocarcinomas, about 50% of adenomas and adenocarcinomas of the colon, about 50% of adenocarcinomas of the lung and carcinomas of the thyroid, and a large fraction of malignancies of the blood such as acute myeloid leukemia and myelodysplastic syndrome have been found to contain activated ras oncogenes. Overall, some 10 to 20% of human tumors have a mutation in one of the three ras genes (H-ras, K-ras, or N-ras).

It is presently believed that inhibiting expression of activated oncogenes in a particular tumor cell might force the cell back into a more normal growth habit. For example, Feramisco et al., *Nature*, 314:639–642, 1985, demonstrated that if cells transformed to a malignant state with an activated ras gene are microinjected with antibody which binds to the protein product of the ras gene, the cells slow their rate of proliferation and adopt a more normal appearance. This has been interpreted as support for the involvement of the product of the activated ras gene in the uncontrolled growth typical of cancer cells.

Antisense oligonucleotide inhibition of oncogenes has proven to be a useful tool in understanding the roles of various oncogene families. "Antisense oligonucleotides" refers to small oligonucleotides which are complementary to the "sense" or coding strand of a given gene, and as a result are also complementary to, and thus able to specifically hybridize with, the mRNA transcript of the gene. Holt et al., *Mol. Cell Biol.*, 8, 963–973, 1988, have shown that antisense oligonucleotides hybridizing specifically with mRNA transcripts of the oncogene c-myc, when added to cultured HL60 leukemic cells, inhibit proliferation and induce differentiation. Anfossi et al., *Proc. Natl. Acad. Sci.*, 86, 3379–3383, 1989, have shown that antisense oligonucleotides specifically hybridizing with mRNA transcripts of the c-myb oncogene inhibit proliferation of human myeloid leukemia cell lines. Wickstrom et al., *Proc. Nat. Acad. Sci.*, 85, 1028–1032, 1988, have shown that expression of the protein product of the c-myc oncogene as well as proliferation of HL60 cultured leukemic cells are inhibited by antisense oligonucleotides hybridizing specifically with c-myc mRNA. U.S. Pat. No. 4,871,838 (Bos et al.) discloses oligonucleotides complementary to a mutation in codon 13 of N-ras to detect said mutation.

In all these cases, instability of unmodified oligonucleotides has been a major problem, as they are subject to degradation by cellular enzymes. PCT/US88/01024 (Zon et al.) discloses phosphorothioate oligonucleotide analogs hybridizable to the translation initiation region of the amplified c-myc oncogene to inhibit HL-60 leukemia cell growth and DNA synthesis in these cells. Tidd et al., *Anti-Cancer Drug Design*, 3, 117–127, 1988, evaluated antisense oligonucleotide methylphosphonate analogs hybridizing specifically to the activated N-ras oncogene and found that while they were resistant to biochemical degradation and were nontoxic in cultured human HT29 cells, they did not inhibit N-ras gene expression and had no effect on these cells. Chang et al., *Anti-Cancer Drug Design*, 4, 221–232, 1989, showed that both methylphosphonate and phosphorothioate analogs of oligonucleotides hybridizing specifically to mRNA transcripts of the Balb-ras gene could inhibit translation of the protein product of this gene in vitro. Because the antisense oligonucleotides and oligonucleotide analogs used by Chang et al. hybridize specifically with the translation initiation region of the ras gene, the binding ability of these oligonucleotides to normal (wild-type) vs. mutated (activated) ras genes was not compared.

The H-ras gene has recently been implicated in a serious cardiac arrhythmia called long Q–T syndrome, a hereditary condition which often causes sudden death if treatment is not given immediately. Frequently there are no symptoms prior to the onset of the erratic heartbeat. Whether the H-ras gene is precisely responsible for long Q–T syndrome is unclear. However, there is an extremely high correlation between inheritance of this syndrome and the presence of a particular variant of the chromosome 11 region surrounding the H-ras gene. This makes the H-ras gene an excellent indicator of increased risk of sudden cardiac death due to the long Q–T syndrome.

There is a great desire to provide compositions of matter which can modulate the expression of the ras gene, and particularly to provide compositions of matter which specifically modulate the expression of the activated form of the ras gene. It is greatly desired to provide methods of diagnosis and detection of the ras gene in animals. It is also desired to provide methods of diagnosis and treatment of conditions arising from ras gene activation. In addition, improved research kits and reagents for detection and study of the ras gene are desired.

OBJECTS OF THE INVENTION

It is an object of the invention to provide oligonucleotides and oligonucleotide analogs which are capable of specifically hybridizing with RNA or DNA deriving from the mammalian ras gene.

It is a further object to provide oligonucleotides and oligonucleotide analogs which are capable of modulating the expression of the ras gene through antisense interaction with the mRNA product of the gene.

Another object of the invention is to provide oligonucleotides and oligonucleotide analogs which are capable of hybridizing selectively to the mRNA of the activated mutant form of the ras gene.

Specific inhibition of expression of the activated form of the ras gene through hybridization of oligonucleotide or oligonucleotide analogs with the mutated codon-12 region of the ras mRNA is yet another object of the invention.

Detection of the mutation from the normal (wild-type) to activated form of the ras gene is another object of the invention.

Differential diagnosis of morphologically similar tumors and identification of high-risk conditions based on the presence of the activated ras gene is yet another object of this invention.

A further object of this invention is to provide methods of diagnosis and treatment of conditions arising due to mutation of the gene from the wild-type to the mutant, activated form of the ras gene.

SUMMARY OF THE INVENTION

In accordance with the present invention, oligonucleotides and oligonucleotide analogs are provided that are specifically hybridizable with DNA or RNA deriving from the human ras gene. The oligonucleotide comprises nucleotide units sufficient in identity and number to effect such specific hybridization. It is preferred that the oligonucleotides or oligonucleotide analogs be specifically hybridizable with the translation initiation codon of the gene, and preferably that the oligonucleotide comprise a sequence CAT. In accordance with another preferred embodiment, oligonucleotides and oligonucleotides that specifically hybridize with codon 12 of the activated H-ras gene are provided, preferably comprising a sequence GAC. In another such embodiment, oligonucleotide or oligonucleotide analogs are provided that specifically hybridize preferentially with the mutated codon 12 of the activated H-ras gene. In this embodiment, such oligonucleotide or oligonucleotide analog preferably comprises a sequence GAC. Such oligonucleotides are conveniently and desirably presented in a pharmaceutically acceptable carrier.

In accordance with other preferred embodiments, the oligonucleotides and oligonucleotide analogs are formulated such that at least some of the linking groups between nucleotide units of the oligonucleotide comprise sulfur-containing species such as phosphorothioate moieties.

Other aspects of the invention are directed to methods for modulating the expression of the human ras gene in cells or tissues and for specifically modulating the expression of the activated ras gene in cells or tissues suspected of harboring a mutation leading to such activation. Additional aspects of the invention are directed to methods of detection of the ras gene in cells or tissues and specific detection of the activated ras gene in cells or tissues suspected of harboring said mutated gene. Such methods comprise contacting cells or tissues suspected of containing the human ras gene with oligonucleotides or oligonucleotide analogs in accordance with the invention in order to interfere with the effect of or detect said gene.

Other aspects of the invention are directed to methods for diagnostics and therapeutics of animals suspected of having a mutation leading to activation of the ras gene. Such methods comprise contacting the animal or cells or tissues or a bodily fluid from the animal with oligonucleotides or oligonucleotide analogs in accordance with the invention in order to modulate the expression of this gene, to treat conditions arising from activation of this gene, or to effect a diagnosis thereof.

BRIEF DESCRIPTION OF THE DRAWINGS

FIG. 5 shows sequences of the oligonucleotides, 5 to 25 nucleotides in length, targeted to the human h-ras mRNA. Two oligonucleotides are targeted to the AUG region and the remainder to the codon-12 region.

The MRNA sequence is written 4' to 3' and the oligonucleotide sequence, 3' to 5' Oligos 2502, 2503, 2570, 2571, 2566 and 2560 correspond to SEQ ID NO: 1 through 6, respectively, but read in the 3' to 5' direction.

Figure 6:
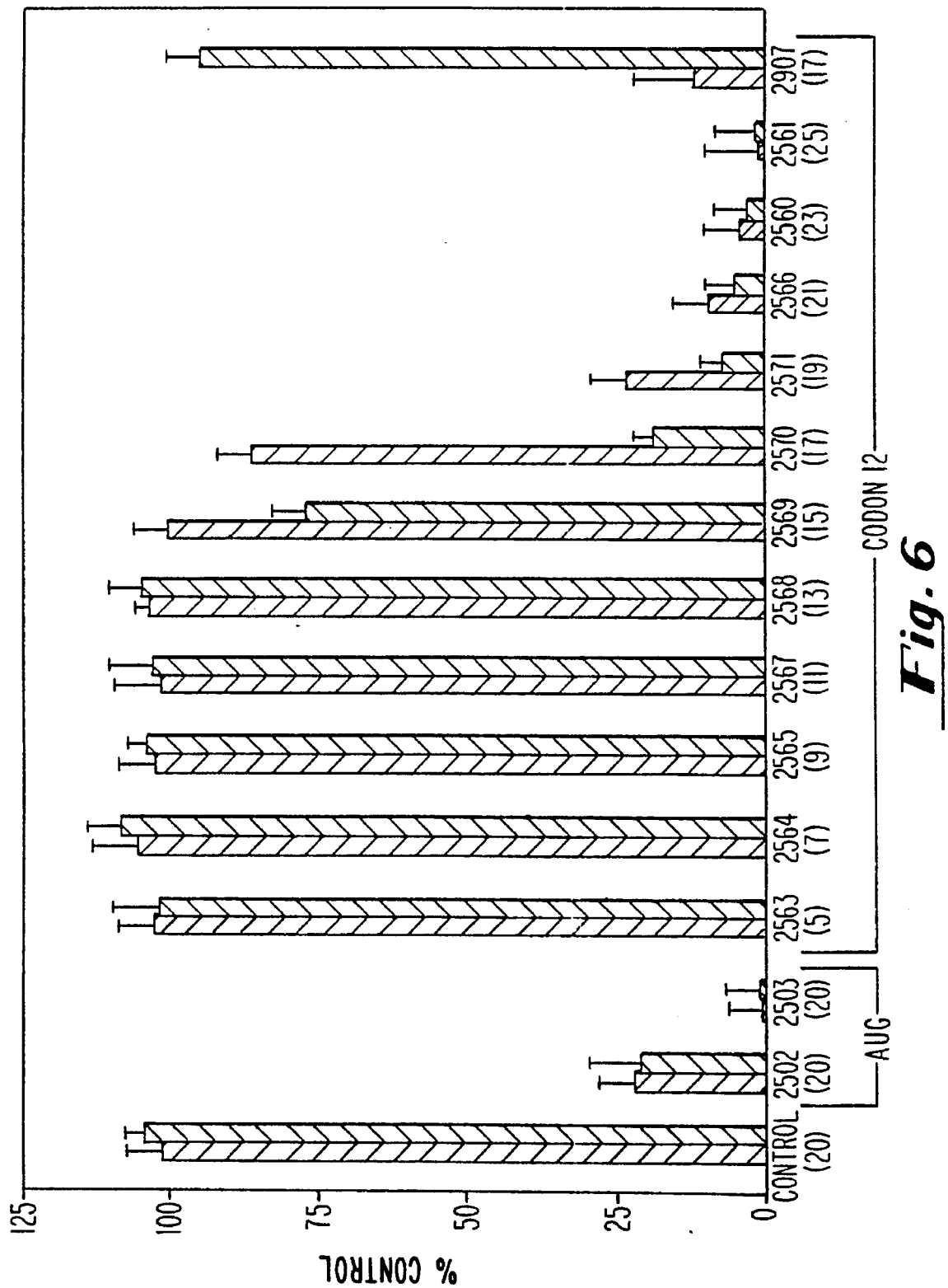
Figure 7A:
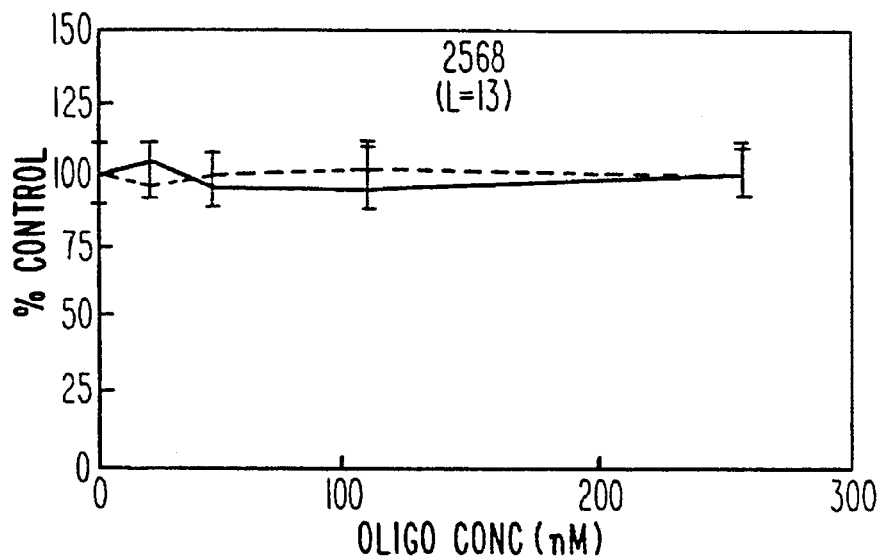
Figure 7B:
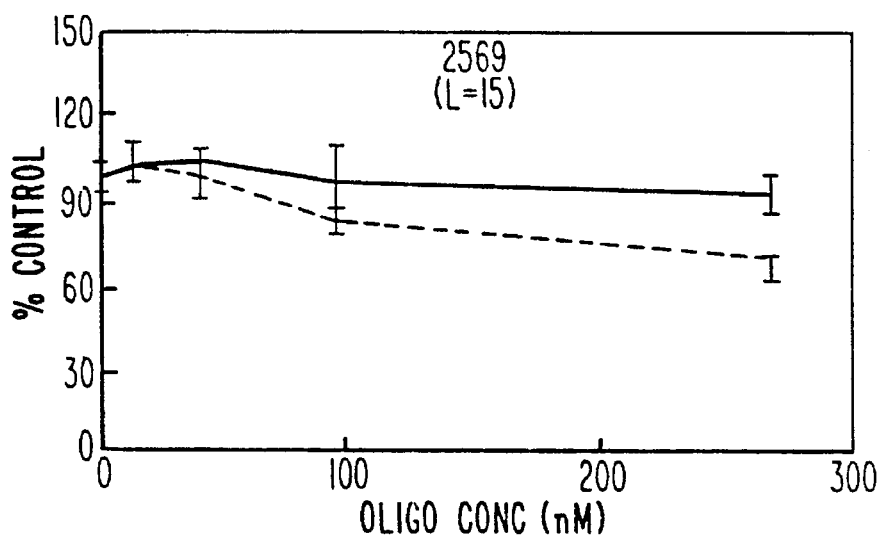
Figure 7C:
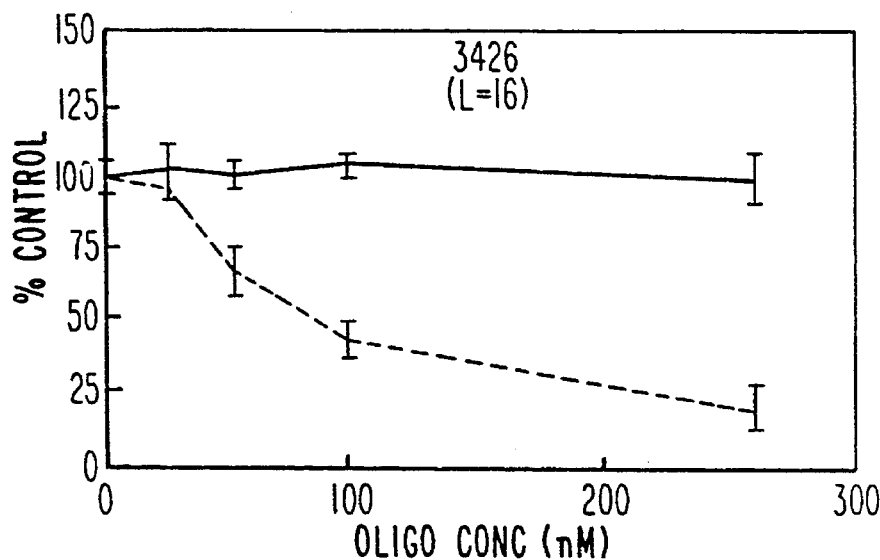
Figure 7G:
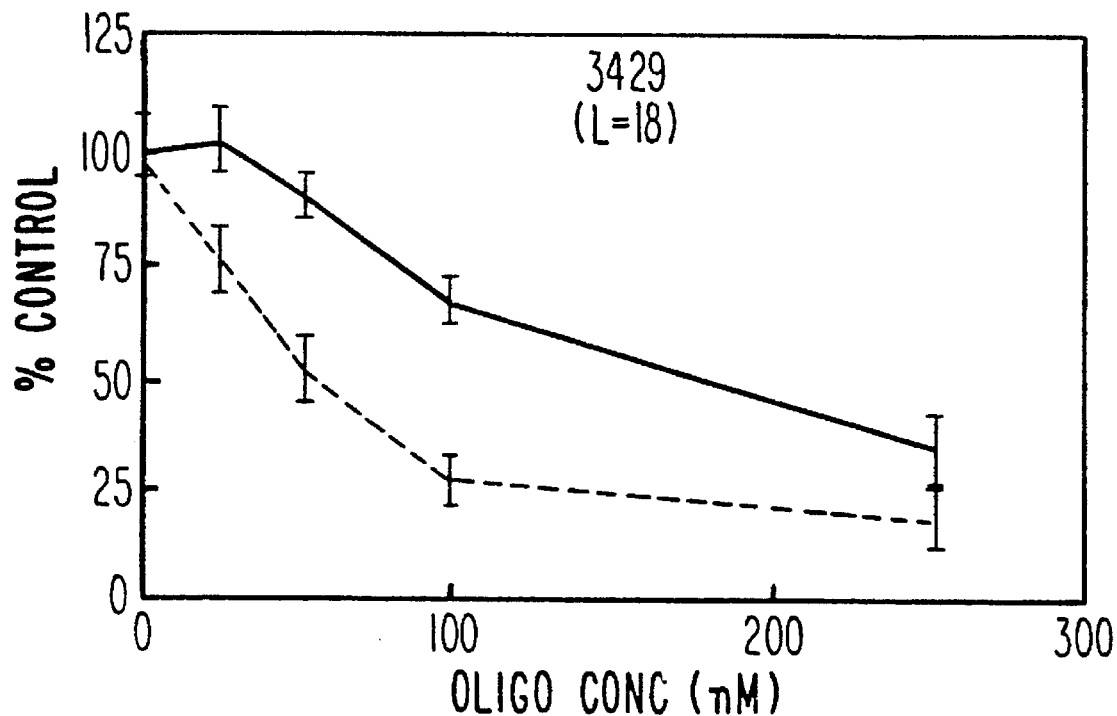
Figure 7H:
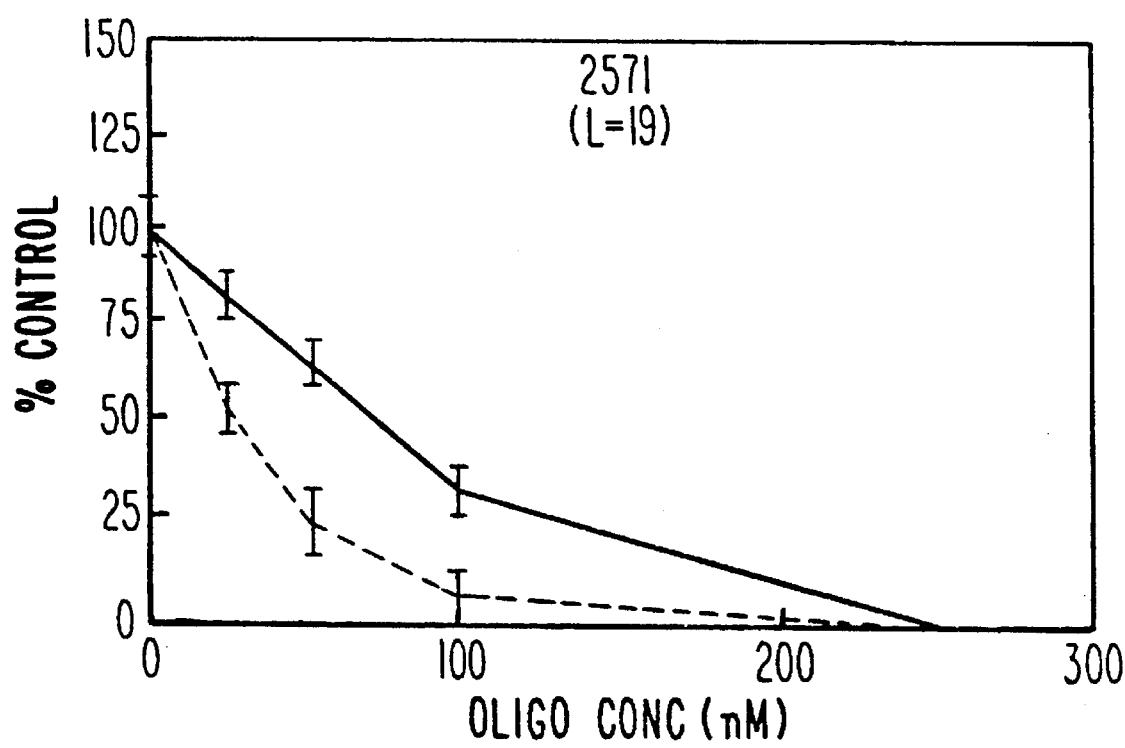

FIG. 6 is a bar graph showing activity (expressed as percent of control) of oligonucleotides from FIG. 5 against wild-type (solid bar) or activated (codon-12 mutant) ras (hatched bar).

FIGS. 7a–7h are 8 panels showing inhibition of ras in a dose-dependent manner. Solid lines are activity against wild-type, dotted lines show activity against activated ras.

Figure 8A:
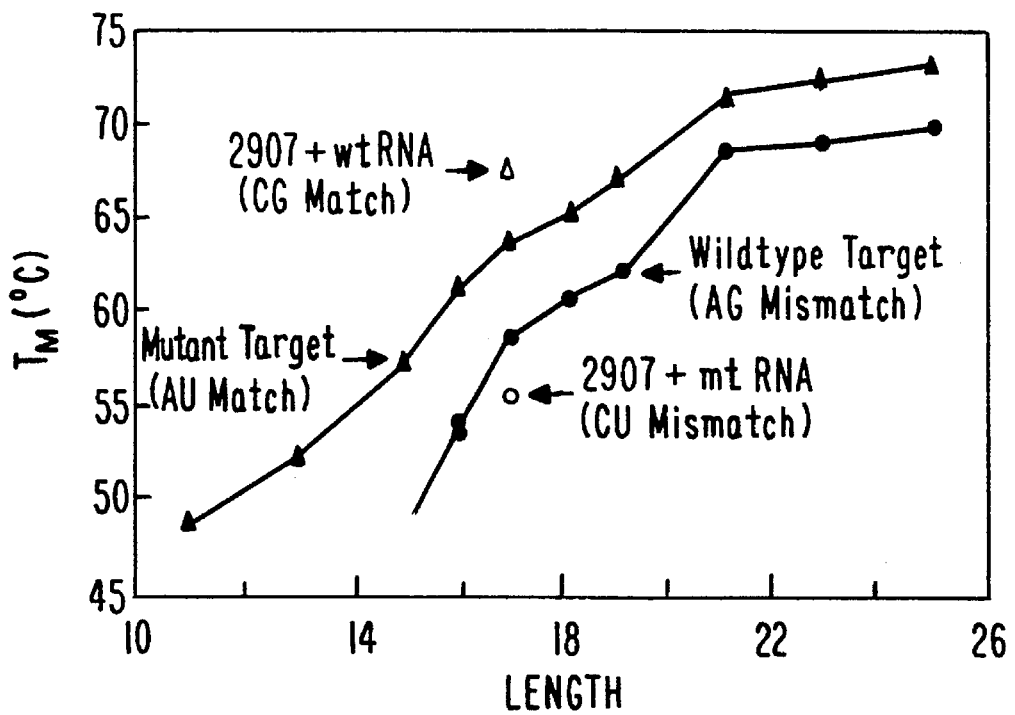
Figure 8B:
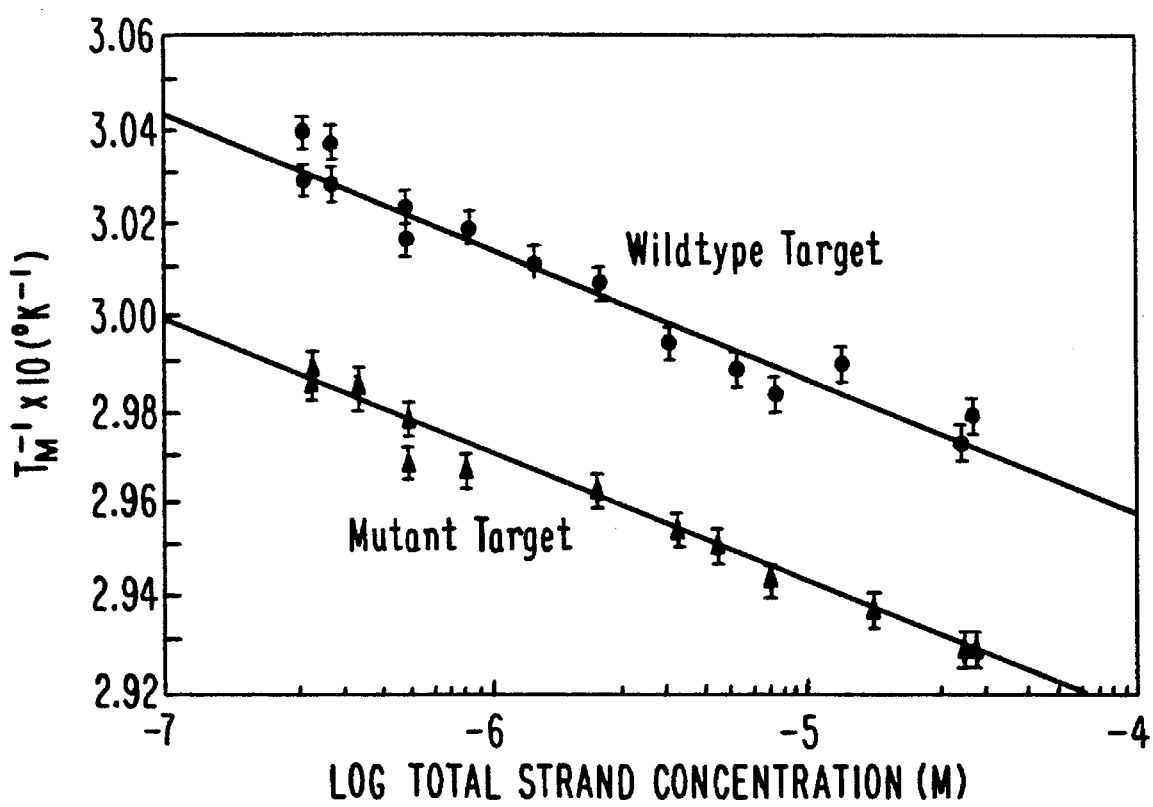

FIG. 8A is a graph showing oligonucleotide length vs Tm.
FIG. 8B is a graph showing oligonucleotide concentration vs. Tm.

Figure 9A:
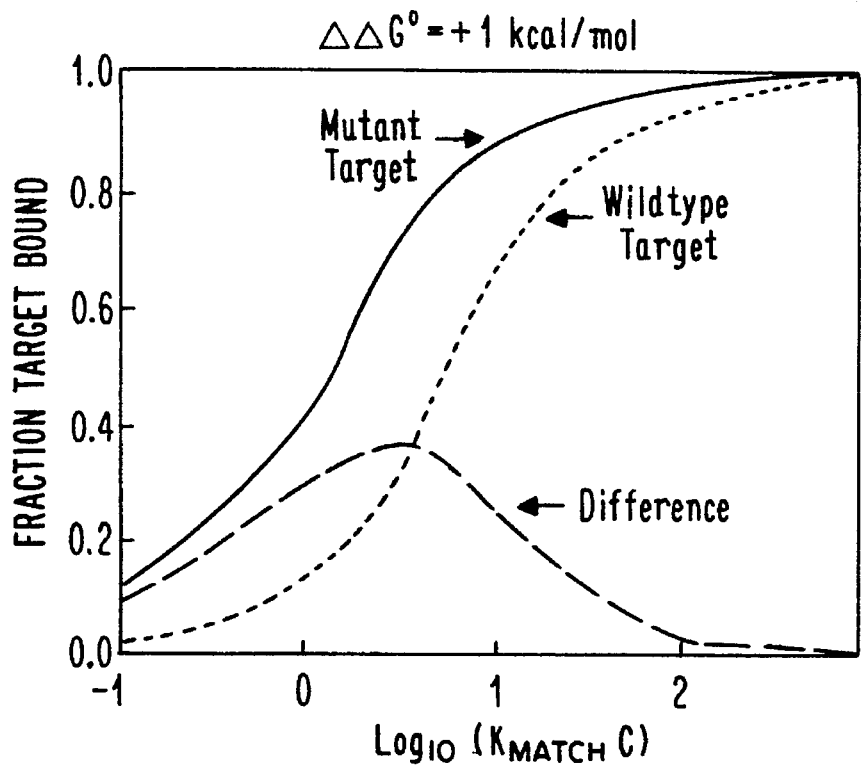
Figure 9B:
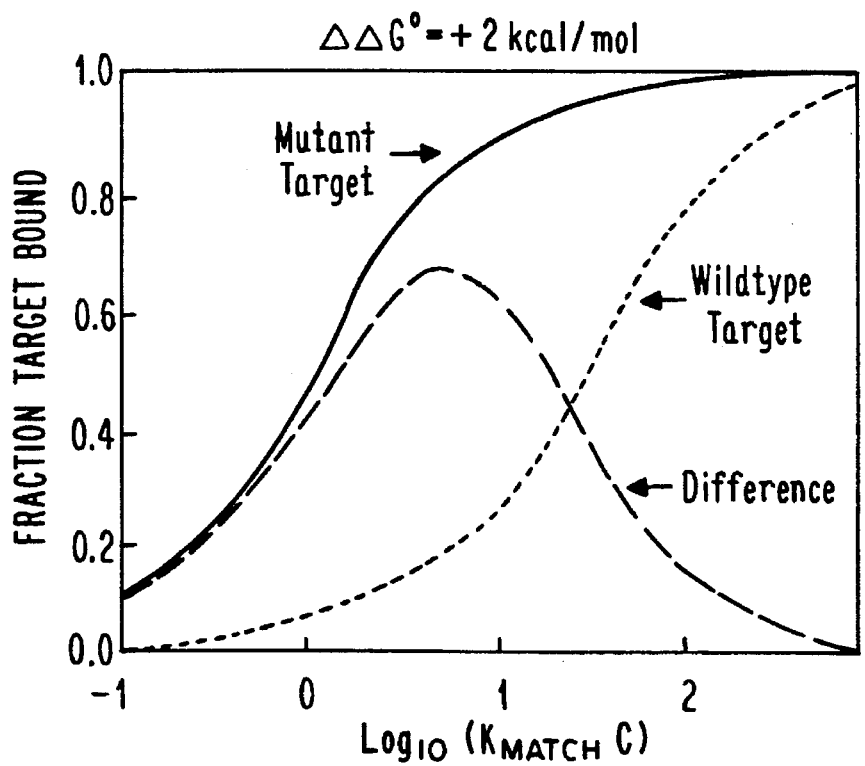
Figure 9C:
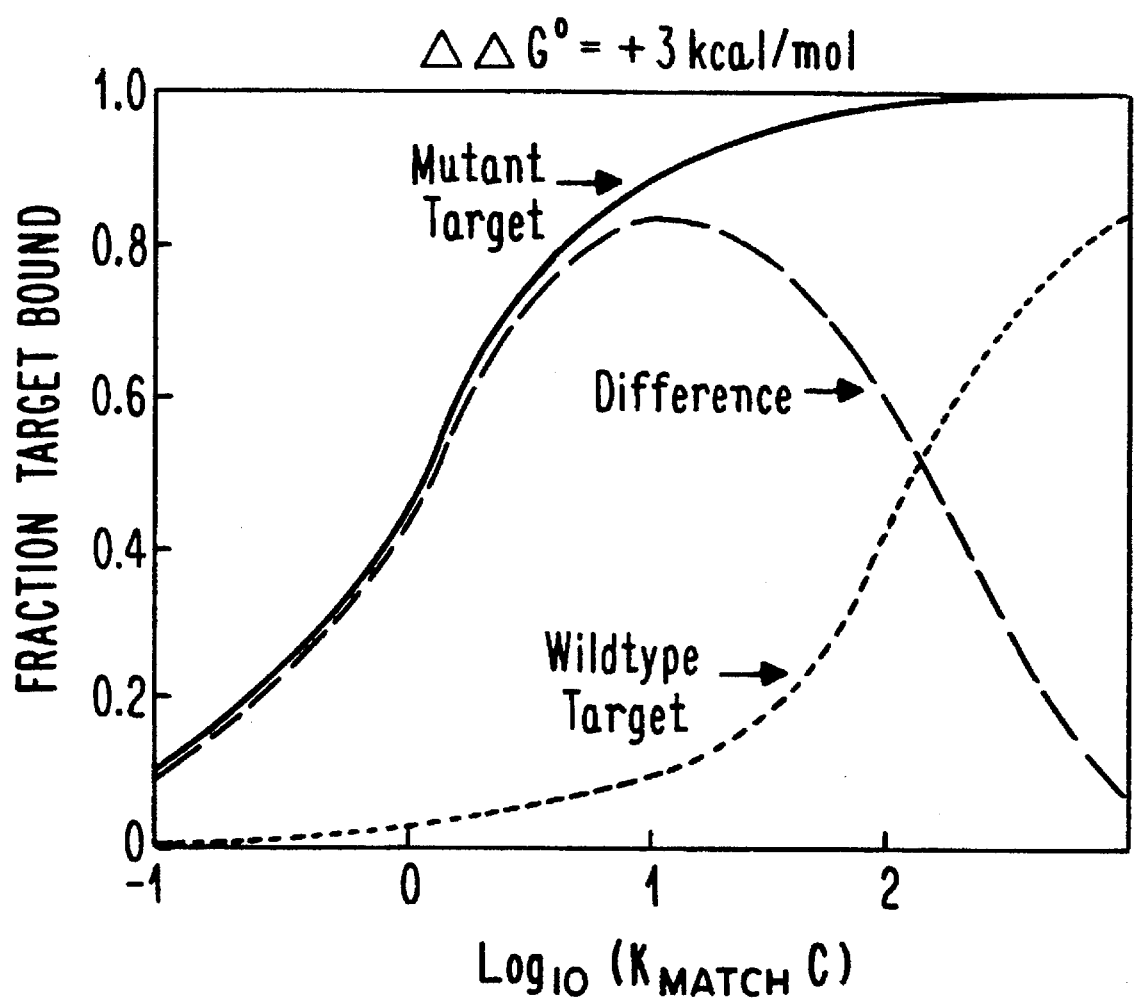

FIG. 9 is a graph showing certain thermodynamic properties of oligonucleotide binding to wild-type and activated (mutant) ras targets.

DETAILED DESCRIPTION OF THE INVENTION

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. In addition, the ability to study cell transformation in carefully controlled, quantitative in vitro assays has led to the identification of specific genes capable of inducing the transformed cell phenotype.

Such cancer-causing genes, or oncogenes, are believed to acquire transformation-inducing properties through mutations leading to changes in the regulation of expression of their protein products. In some cases such changes occur in non-coding DNA regulatory domains, such as promoters and enhancers, leading to alterations in the transcriptional activity of oncogenes, resulting in over- or under-expression of their gene products. In other cases, gene mutations occur within the coding regions of oncogenes, leading to the production of altered gene products that are inactive, overactive, or exhibit an activity that is different from the normal (wild-type) gene product.

To date, more than 30 cellular oncogene families have been identified. These genes can be categorized on the basis of both their subcellular location and the putative mechanism of action of their protein products. The ras oncogenes are members of a gene family which encode related proteins that are localized to the inner face of the plasma membrane. ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins known as GTP binding proteins, or G proteins, suggest that ras gene products play a fundamental role in basic cellular regulatory functions relating to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon 12 of the H-ras gene in which a base change from GGC to GTC results in a glycine-to-valine substitution in the GTPase regulatory domain of the ras protein product. This single amino acid change is thought to abolish normal control of ras protein function, thereby converting a normally regulated cell protein to one that is continuously active. It is believed that such deregulation of normal ras protein function is responsible for the transformation from normal to malignant growth.

The present invention provides oligonucleotides and oligonucleotide analogs for inhibition of human ras gene expression. The invention also provides oligonucleotides and oligonucleotide analogs for selective inhibition of expression of the mutant form of ras.

In the context of this invention, the term "oligonucleotide" refers to a plurality of joined nucleotide units formed from naturally-occurring bases and furanosyl groups joined by native phosphodiester bonds. This term effectively refers to naturally-occurring species or synthetic species formed from naturally-occurring subunits.

"Oligonucleotide analog," as that term is used in connection with this invention, refers to moieties which function similarly to oligonucleotides but which have non-naturally occurring portions. Thus, oligonucleotide analogs may have altered sugar moieties or inter-sugar linkages. Exemplary among these are the phosphorothioate and other sulfur-containing species which are known for use in the art. They may also comprise altered base units or other modifications consistent with the spirit of this invention.

In accordance with certain preferred embodiments, at least some of the phosphodiester bonds of the oligonucleotide have been substituted with a structure which functions to enhance the ability of the compositions to penetrate into the region of cells where the RNA whose activity is to be modulated is located, and to make the compositions more resistant to degradation by cellular enzymes. It is preferred that such linkages be sulfur-containing. It is presently preferred that such substitutions comprise phosphorothioate bonds. Others such as alkyl phosphorothioate bonds, N-alkyl phosphoramidites, phosphorodithioates, alkyl phosphonates, and short chain alkyl or cycloalkyl structures may also be useful. In accordance with other preferred embodiments, the phosphodiester bonds are substituted with structures which are, at once, substantially non-ionic and non-chiral, or, alternatively, with structures that are sequence-specific and substantially chiral. Persons of ordinary skill in the art will be able to select other linkages for use in the practice of the invention.

Oligonucleotide analogs may also include species which include at least some modified base forms. Thus, purines and pyrimidines other than those normally found in nature may be so employed. In accordance with one such embodiment, one or more bases comprises 2-(amino)adenine. In other such embodiments, one or more bases comprises 2-(methylamino)adenine, 2-(alkylamino)adenine, 2-(imidazolylalkyl)adenine, 2-(aminoalkylamino)adenine or other heterosubstituted alkyladenines. Similarly, modifications on the furanose portions of the nucleotide subunits may also occur as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to hybridize with the ras gene or mRNA deriving from it to inhibit the function or expression of the ras gene.

The oligonucleotides and oligonucleotide analogs in accordance with this invention preferably comprise from about 10 to about 30 subunits. It is more preferred that such oligonucleotides and analogs comprise from about 15 to about 25 subunits. As will be appreciated, a subunit is a base and sugar combination suitably bound to adjacent subunits through phosphodiester or other bonds.

The oligonucleotides and oligonucleotide analogs of this invention are designed to be hybridizable with messenger RNA derived from the H-ras gene. Such hybridization, when accomplished, interferes with the normal roles of the messenger RNA to cause a loss of its function in the cell. The functions of messenger RNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with the RNA function is to interfere with expression of the H-ras gene. The protein products of the other mammalian ras genes, N-ras and K-ras, are identical to H-ras over the first 85 amino acids. The nucleic acid sequences of the three ras genes, while not identical, are known, and persons of ordinary skill in the art will be able to use this invention as a guide in preparing oligonucleotides or oligonucleotide analogs specifically hybridizable with the N-ras and K-ras genes.

The oligonucleotides and oligonucleotide analogs of this invention can be used in diagnostics, therapeutics and as research reagents and kits. Since the oligonucleotides and oligonucleotide analogs of this invention hybridize to the ras gene, sandwich and other assays can easily be constructed to exploit this fact. Furthermore, since the oligonucleotides and oligonucleotide analogs of this invention hybridize preferentially to the mutant (activated) form of the ras oncogene, such assays can be devised for screening of cells and tissues for ras conversion from wild-type to activated form. Such assays can be utilized for differential diagnosis of morphologically similar tumors, and for detection of increased risk of cancer stemming from ras gene activation. Provision of means for detecting hybridization of oligonucleotide or analog with the ras gene can routinely be accomplished. Such provision may include enzyme conjugation, radiolabelling or any other suitable detection systems. Kits for detecting the presence or absence of ras or activated ras may also be prepared.

The following examples illustrate the present invention and are not intended to limit the same.

EXAMPLES

Example 1

Oligonucleotide synthesis: Unmodified oligonucleotides were synthesized on an automated DNA synthesizer (Applied Biosystems model 380B) using standard phosphoramidite chemistry with oxidation by iodine. For phosphorothioate oligonucleotides, the standard oxidation bottle was replaced by 0.2M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitation twice out of 0.5M NaCl solution with 2.5 volumes ethanol. Analytical gel electrophoresis was accomplished in 20% acrylamide, 8M urea, 454 mM Tris-borate buffer, pH=7.0. Oligonucleotides and phosphorothioates were judged from polyacrylamide gel electrophoresis to be greater than 80% full-length material.

Example 2 ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon 12) and non-mutant (wild-type) human H-ras genes. H-ras gene templates were purchased from the American Type Culture Collection (ATCC numbers 41000 and 41001) in Bethesda, Md. The oligonucleotide PCR primers 5'-ACA-TTA-TGC-TAG-CTT-TTT-GAG-TAA-ACT-TGT-GGG-GCA-GGA-GAC-CCT-GT-3' (sense), SEQ ID NO: 7, and 5' -GAG-ATC-TGA-AGC-TTC-TGG-ATG-GTC-AGC-GC-3' (antisense), SEQ ID NO: 8, were used in standard PCR reactions using mutant and non-mutant H-ras genes as templates. These primers are expected to produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were 5'-GAG-ATC-TGA-AGC-TTG-AAG-ACG-CCA-AAA-ACA-TAA-AG-3' (sense), SEQ ID NO: 9, and 5'-ACG-CAT-CTG-GCG-CGC-CGA-TAC-CGT-CGA-CCT-CGA-3' (antisense), SEQ ID NO: 10, were used in standard PCR reactions using a commercially available plasmid (pT3/T7-Luc) (Clontech), containing the luciferase reporter gene, as a template. These primers were expected to yield a product of approximately 1.9 kb corresponding to the luciferase gene, flanked by HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter.

Example 3

Transfection of Cells with Plasmid DNA

Transfections were performed as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY, with the following modifications. HeLa cells were plated on 60 mm dishes at $5 \times 10^5$ cells/dish. A total of 10 μg of DNA was added to each dish, of which 9 μg was ras-luciferase reporter plasmid and 1 μg was a vector expressing the rat glucocorticoid receptor under control of the constitutive Rous sarcoma virus (RSV) promoter. Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells were pretreated with antisense oligonucleotides prior to activation of reporter gene expression by dexamethasone.

Example 4

Oligonucleotide Treatment of Cells

Immediately following plasmid transfection, cells were washed three times with Opti-MEM (Gibco), prewarmed to 37° C. Two ml of Opti-MEM containing 10 μg/ml N-[1-(2, 3-dioleyloxy)propyl]-N,N,N,-trimethylammonium chloride (DOTMA) (Bethesda Research Labs, Gaithersburg, Md.) was added to each dish and oligonucleotides were added directly and incubated for 4 hours at 37° C. Opti-MEM was then removed and replaced with the appropriate cell growth medium containing oligonucleotide. At this time, reporter gene expression was activated by treatment of cells with dexamethasone to a final concentration of 0.2 μM. Cells were harvested 12–16 hours following steroid treatment.

Example 5

Luciferase Assays

Luciferase was extracted from cells by lysis with the detergent Triton X-100, as described by Greenberg, M. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. A Dynatech ML1000 luminometer was used to measure peak luminescence upon addition of luciferin (Sigma) to 625 μM. For each extract, luciferase assays were performed multiple times, using differing amounts of extract to ensure that the data were gathered in the linear range of the assay.

Example 6

Antisense Oligonucleotide Inhibition of ras-Luciferase Gene Expression

A series of antisense phosphorothioate oligonucleotide analogs targeted to either the H-ras translation initiation codon or the codon-12 point mutation of activated H-ras were screened using the ras-luciferase reporter gene system described in the foregoing examples. Of this initial series, six oligonucleotides were identified that gave significant and reproducible inhibition of ras-luciferase activity. The base sequences, sequence reference numbers and sequence ID numbers of these oligonucleotides (all are phosphorothioate analogs) are shown in Table 1.

TABLE 1

| Oligo ref. no. | Sequence | SEQ ID ID NO: |
|---|---|---|
| 2502 | CTT—ATA—TTC—CGT—CAT—CGC—TC | 1 |
| 2503 | TCC—GTC—ATC—GCT—CCT—CAG—GG | 2 |
| 2570 | CCA—CAC—CGA—CGG—CGC—CC | 3 |
| 2571 | CCC—ACA—CCG—ACG—GCG—CCC—A | 4 |
| 2566 | GCC—CAC—ACC—GAC—GGC—GCC—CAC | 5 |
| 2560 | TGC—CCA—CAC—CGA—CGG—CGC—CCA—CC | 6 |

Figure 1:
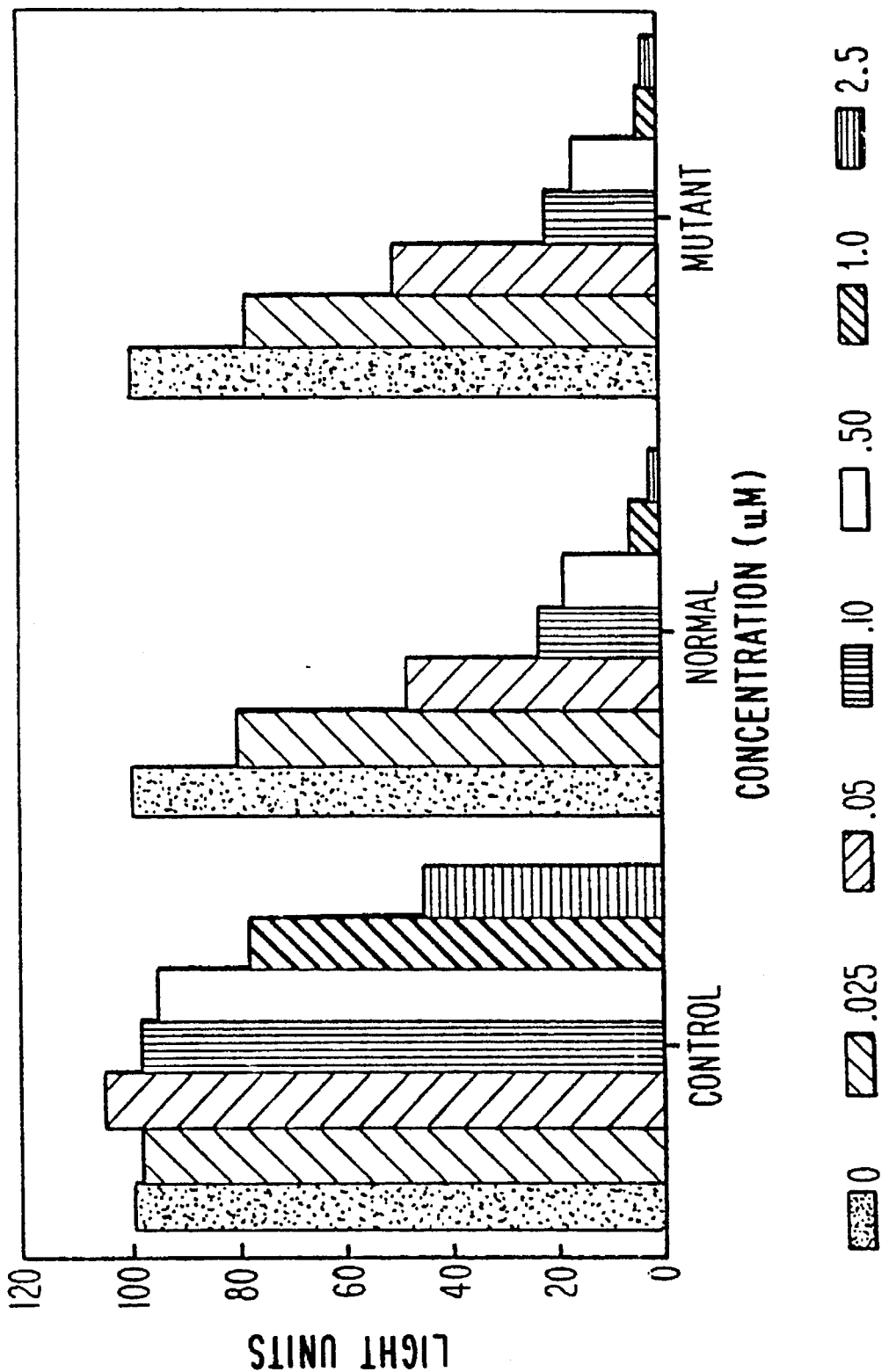
FIG. 1 is a bar graph showing dose-response inhibition of ras-luciferase fusion protein expression using oligonucleotides targeted to the H-ras translation initiation codon (AUG). Expression is measured by measurement of luciferase activity as assayed by amount of light emitted when luciferin is added.

FIG. 1 shows a dose-response experiment in which cells expressing either the normal ras-luciferase reporter gene or the mutant ras-luciferase reporter gene were treated with increasing concentrations of the phosphorothioate oligonucleotide analog 2503 (sequence I.D. no. 2). This compound is targeted to the translational initiation codon of H-ras RNA transcripts. As shown in FIG. 1, treatment of cells with this oligonucleotide resulted in a dose-dependent inhibition of ras-luciferase activity, displaying IC50 values of approximately 50 nM for both the normal and the mutant ras targets. The control oligonucleotide is a random phosphorothioate oligonucleotide analog, 20 bases long. Results are expressed as percentage of luciferase activity in transfected cells not treated with oligonucleotide. The observation that an oligonucleotide targeted to the ras translation initiation codon is equally effective in reducing both mutant and normal ras expression is expected since the two targets have identical sequence compositions in the region surrounding the AUG translation initiation site.

Figure 2:
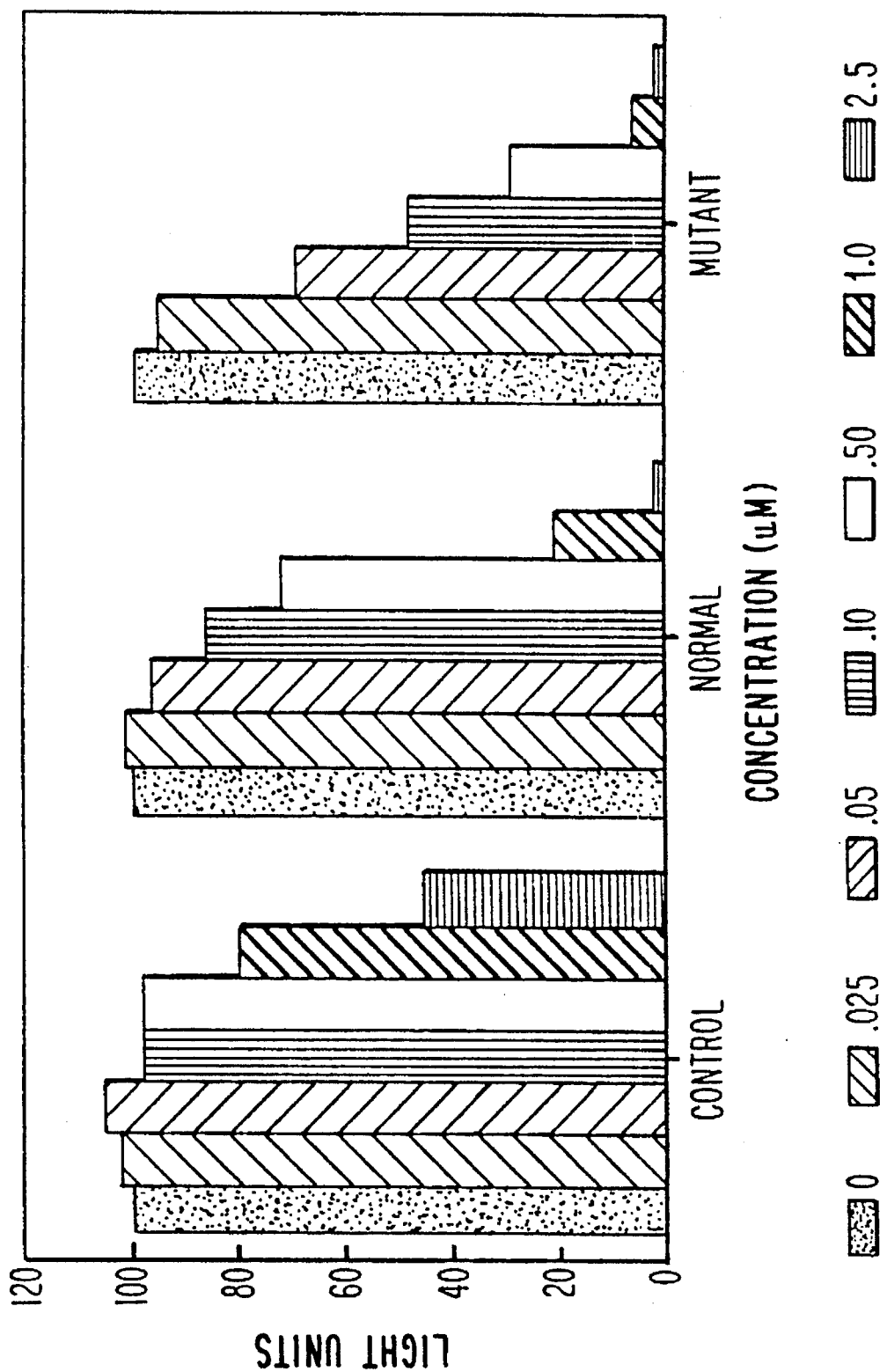
FIG. 2 is a bar graph showing dose-response inhibition of ras-luciferase fusion protein expression using oligonucleotides targeted to the mutated codon-12 region in activated H-ras. Expression is measured by measurement of luciferase activity as assayed by amount of light emitted when luciferin is added.

FIG. 2 shows a dose-response experiment in which cells were treated with phosphorothioate oligonucleotide analog 2570 (sequence I.D. no. 3), a compound that is targeted to the codon-12 point mutation of mutant (activated) H-ras RNA. The control oligonucleotide is a random phosphorothioate oligonucleotide analog, 20 bases long. Results are expressed as percentage of luciferass activity in transfected cells not treated with oligonucleotide. As the figure shows, treatment of cells with increasing concentrations of this oligonucleotide resulted in a dose-dependent inhibition of ras-luciferase activity in cells expressing either the mutant form or the normal form of ras-luciferase. However, careful examination of the data shows that at low concentrations, oligonucleotide 2570 displayed approximately threefold selectivity toward the mutant form of ras-luciferase as compared to the normal form. In fact, 2570 displayed an IC50 value for the mutant form of ras-luciferase of approximately 100 nM whereas the same compound displayed in IC50 value of approximately 250 nM for the unmutated form.

Figure 3:
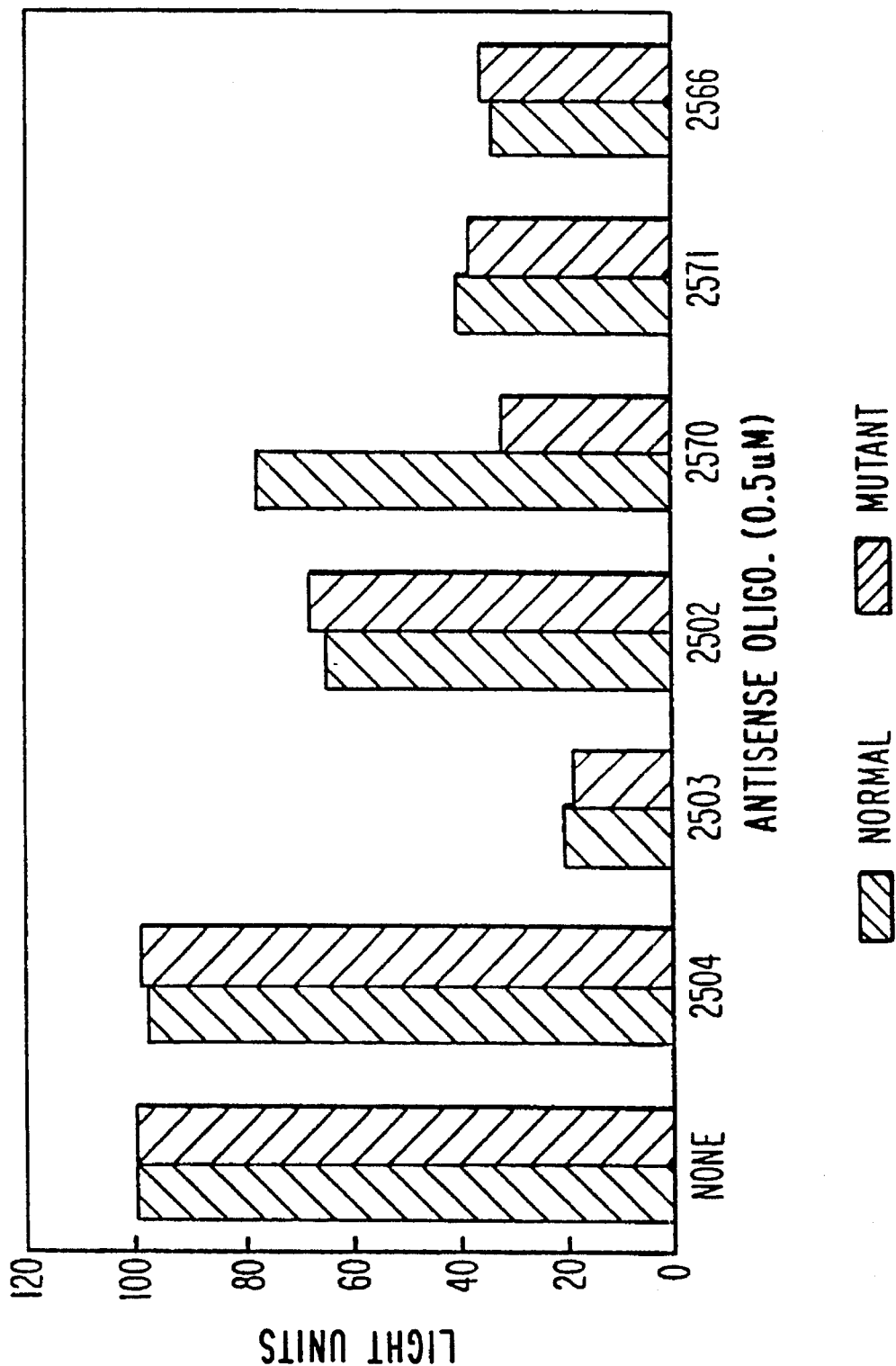
FIG. 3 is a bar graph showing single-dose inhibition of ras-luciferase fusion protein expression by antisense phosphorothioate compounds. Expression is measured by measurement of luciferass activity as assayed by amount of light emitted when luciferin is added.
Figure 4B:
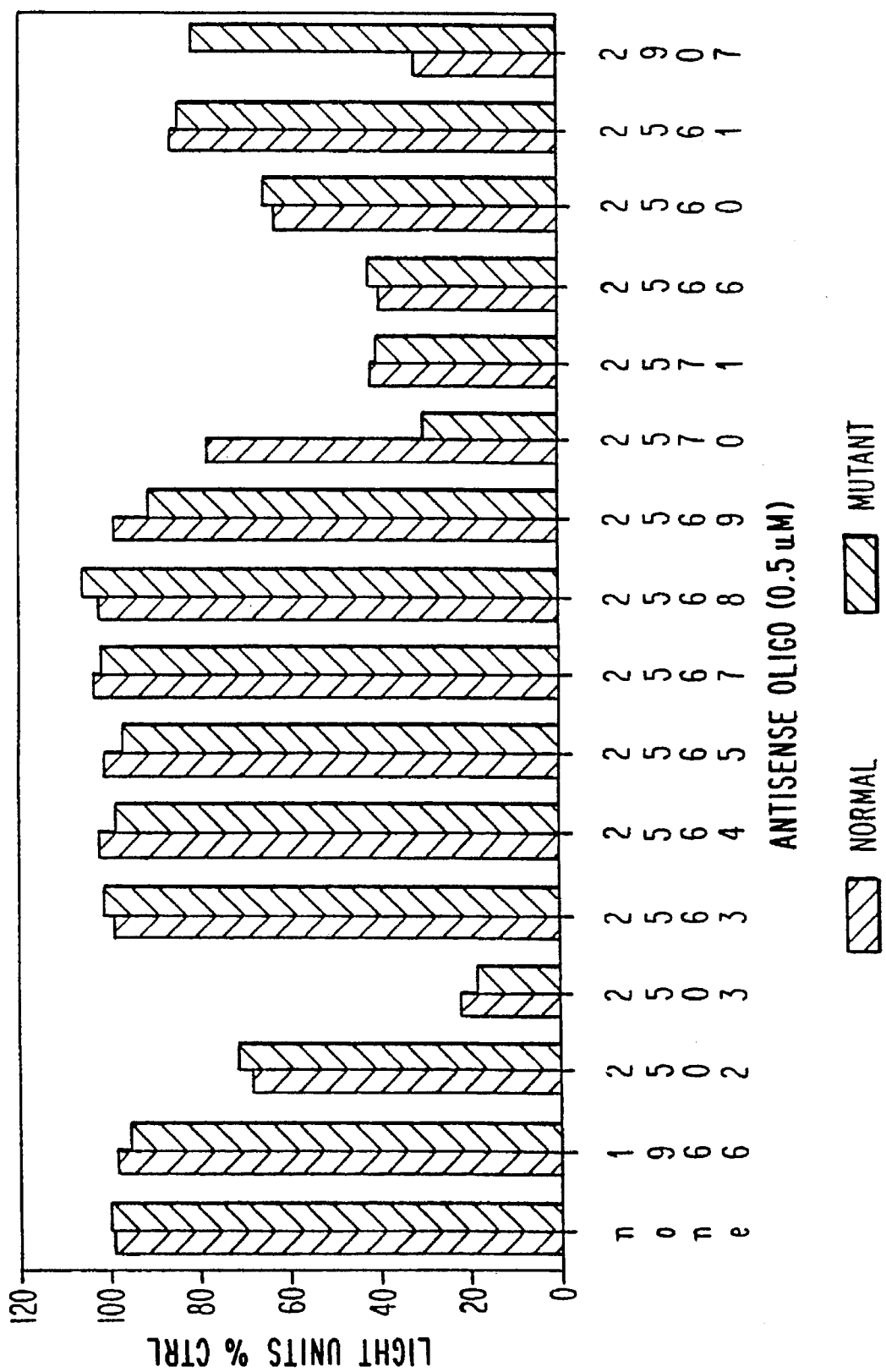
FIG. 4 is a table and bar graph summarizing data obtained for 13 antisense oligonucleotides specifically hybridizable with the activated H-ras gene. Shown for each oligonucleotide is its length, region of the activated ras gene to which it specifically hybridizes, and its activity in inhibiting expression of the ras-luciferase fusion protein.

FIG. 3 shows the results of a typical experiment in which cells expressing either the normal form or the mutant form of ras-luciferase were treated with a single dose (0.5 μM) of oligonucleotide targeted to either the translation initiation codon of H-ras or the codon-12 point mutation. The antisense phosphorothioate oligonucleotide analogs tested are shown in Table 1. The control oligonucleotide (2504) is a random phosphorothioate oligonucleotide analog, 20 bases long. Results are expressed as percentage of luciferass activity in transfected cells not treated with oligonucleotide. As shown in FIG. 3, compound 2503 (sequence I.D. no. 2), targeted to the ras translational initiation codon, was most effective in inhibiting ras-luciferase activity. Of the three compounds targeted to the codon-12 point mutation of activated H-ras, only the 17-mer oligonucleotide 2570 (sequence I.D. no. 3) displayed selectivity toward the mutated form of ras-luciferase as compared to the normal form. This is also shown in FIG. 4, which summarizes data obtained with all 13 antisense oligonucleotides complementary to the activated H-ras gene, as well as a scrambled control oligonucleotide (1966) and a control oligonucleotide (2907) complementary to the codon-12 region of wild-type ras. Shown for each oligonucleotide is its length, region to which it is complementary, and its activity in suppressing expression of the ras-luciferase fusion protein. The longer phosphorothioates targeted to the codon-12 point mutation, while displaying substantial antisense activity toward ras-luciferase expression, did not demonstrate selective inhibition of expression of the mutant form of ras-luciferase. Phosphorothioate oligonucleotides targeted to the codon-12 point mutation that were less than 17 nucleotides in length did not show activity to either form of ras-luciferase. These results demonstrate effective antisense activity of Phosphorothioate oligonucleotides targeted to ras sequences.

Example 7

Synthesis of 2-(amino)adenine-substituted oligonucleotides

Oligonucleotides and phosphorothioate oligonucleotide analogs will be synthesized as in Example 1, with the following exception: at positions at which a 2-(amino)adenine is desired, the standard phosphoramidite is replaced with a commercially available 2-aminodeoxyadenosine phosphoramidite (ChemGenes).

Example 8

2-(Amino)adenine-Modified Antisense Oligonucleotide Inhibition of ras-Luciferase Gens Expression A series of antisense phosphorothioate oligonucleotide analogs complementary to the codon-12 point mutation of activated ras will be synthesized as described in Example 7, having a 2-(amino)adenine at the position complementary to the uracil of the mutated codon 12. Because the amino group at the 2-position of the adenins is able to hydrogen-bond with the oxygen in the 2-position on the uracil, three hydrogen bonds instead of the usual two are formed. This serves to greatly stabilize the hybridization of the 2-(amino)adenine-modified antisense oligonucleotide to the activated ras gene while destabilizing, or having no net effect, on the stability of this oligo to the wild-type codon 12, because of the modified A–G mismatch at this position.

Example 9

Additional antisense oligonucleotide inhibition of ras-luciferase gene expression AUG target To identify antisense oligonucleotides capable of optimally and selectively inhibiting expression of mutant H-ras mRNA relative to wild type H-ras, a series of eleven phosphorothioate oligonucleotides, ranging in length between 5 and 25 bases, were tested for inhibition of mutant and wild type ras-luciferase in transient transfection assays. In addition, two 20-base phosphorothioate oligonucleotides, targeted to the H-ras AUG codon, were designed and tested (FIG. 5). These thirteen oligonucleotides were tested initially for inhibition of ras-luciferase expression at a single dose (100 nM) in HeLa cells. The cells were pretreated for 4 hour with oligonucleotide plus cationic lipid (as described in Example 4) to enhance cellular uptake. As shown in FIG. 6, both AUG-targeted oligonucleotides were effective in inhibiting ras-luciferase expression.

Codon-12 target: Oligonucleotides targeted to the H-ras codon 12 point mutation also were effective in inhibiting expression of ras-luciferase. Oligonucleotides 15 bases or greater in length were active against the mutant H-ras target. Above 15 bases in length, antisense activity increased with oligonucleotide chain length under these conditions. Selective inhibition of mutant over wild type ras-luciferase expression was also observed. The 17-mer 2570 showed a four-fold inhibition of mutant ras-luciferase relative to wild-type. In order to demonstrate that 2570 was acting in a sequence-specific manner, a variant of this compound was tested (2907) in which the central adenosine residue was replaced with cytosine, making this oligonucleotide perfectly complementary to the wild type H-ras target. Hence, this oligonucleotide will contain a single mismatch at the center of the oligonucleotide/RNA duplex when fully hybridized to the mutant H-ras sequence. As shown in FIG. 6, oligonucleotide 2907 gave a five-fold inhibition of wild type ras-luciferase relative to mutant ras-luciferase.

Two 16mers and two 18mers were designed and tested (FIG. 6). FIG. 7 shows the results of an experiment in which antisense activity and mutant selectivity was determined for oligonucleotides of length 13, 15, 16, 17, 18 and 19 bases in a dose-dependent manner. The results demonstrate that all of these compounds except the 13-mer displayed activity against H-ras sequences and showed some degree of selectivity for the mutant over the wild-type sequence. Oligonucleotides of length 16 and 17 bases displayed the greatest selectivity (4- and 5-fold, respectively) under these conditions.

Example 10

Melting curves

Absorbance vs temperature curves were measured at 260 nm using a Gilford 260 spectrophotometer interfaced to an IBM PC computer and a Gilford Response II spectrophotometer. The buffer contained 100 mM Na$^+$, 10 mM phosphate and 0.1 mM EDTA, pH 7. Oligonucleotide concentration was 4 μM each strand determined from the absorbance at 85° C. and extinction coefficients calculated according to Puglisi and Tinoco. *Methods in Enzymol.* 1989, 180, 304–325. $T_m$ values, free energies of duplex formation and association constants were obtained from fits of data to a two state model with linear sloping baselines. Petersheim, M. and Turner, D. H. (1983) *Biochemistry* 1983, 22,256–263. Reported parameters are averages of at least three experiments. For some oligonucleotides, free energies of duplex formation were also obtained from plots of $T_m^{-1}$ vs $\log_{10}$(concentration). Borer, P. N., Dengler, B., Tinoco, I., Jr., and Uhlenbeck, O. C., *J. Mol. Biol.*, 1974, 86, 843–853.

Example 11

Hybridization of phosphorothioate antisense oligonucleotides to single stranded 25met RNA targets FIG. 5 shows the sequences of 15 phosphorothioate oligonucleotides each targeted to H-ras mRNA containing the codon 12 G→U point mutation. These oligonucleotides range between 5 and 25 bases in length and are centered around the point mutation. Melting temperatures for these antisense phosphorothioates against mutant and wild type 25mer RNA targets at 4 μM strand concentration are plotted in FIG. 8. $T_m$ of these oligonucleotides increased with increasing chain length and $T_m$ for hybridization to the mutant target was greater than that for the wild type target. Oligonucleotide 2907 is a phosphorothioate 17-mer variant of 2570 in which the central adenosine residue was replaced with cytosine, making this oligonucleotide perfectly complementary to the wild type H-ras target. As expected, the melting temperature for hybridization of this oligonucleotide to the wild type target was greater than that for the mutant target, which now contains a single mismatch in the oligonucleotide/RNA duplex at the site of the point mutation. For the 17mer phosphorothioate that is perfectly complementary to the mutant H-ras target (2570), thermodynamic parameters were also obtained from dependence of $T_m$ on oligonucleotide concentration (FIG. 9). These data were used to determine the free energy difference ($\Delta\Delta G°_{37}$) between hybridization of oligonucleotides to the mutant target and to the wild type target.

The degree of selectivity that can be achieved theoretically for targeting mutant over wild type H-ras increases significantly as $\Delta\Delta G°_{37}$ increases. Chemical modification of the antisense strand may increase $\Delta\Delta G°_{37}$ and therefore enhance selectivity. For example, Helene and coworkers (Saison-Behmoaras et al., (1991) EMBO J. 10:1111–1118) used an intercalating agent tethered to an antisense oligonucleotide to increase selectivity. Other possibilities include modified nucleosides such as 2-(amino)adenosine (i.e., 2,6 diaminopurine riboside), which may bind more tightly than dA to U and less tightly than dA to G, thus increasing $\Delta\Delta G°_{37}$ for the A·U→A·G mismatch.

By utilizing the teachings of this invention, targeting of other point mutations may also allow for a greater $\Delta\Delta G°_{37}$ and hence greater selectivity. It has been found that $\Delta\Delta G°_{37}$ ranges from 1–2 kcal/mol for the most stable mismatches to 5–6 kcal/mol for the least stable mismatches. When possible, therefore, to maximize selectivity for the mutant target, mutations that generate stable mismatches (e.g. G→A) are less preferred than mutations that generate unstable mismatches (e.g. C→G, U→G, A→C). An example of this can be found in the autosomal dominant mutations associated with familial Alzheimer's disease. Three different point mutations of the β-amyloid precursor gene have been shown to cosegregate with this disease. These mutations include G→A ($\Delta\Delta G°_{37}$=+1.2 kcal/mol), G→T ($\Delta\Delta G°_{37}$=+3.9 kcal/mol), and T→G ($\Delta\Delta G°_{37}$=+6.3 kcal/mol)[2]. In this case, targeting the T–G mutation is predicted to yield the greatest selectivity for mutant β-amyloid by an antisense oligonucleotide.

It may be possible to obtain selectivity by taking advantage of the substrate requirements of RNaseH. Chimeric oligonucleotides containing 2'-O-methyl ribonucleotide/deoxyribonucleotide linkages have been shown to direct RNase H cleavage to specific sites within the hybridized RNA strand as per the teachings of U.S. patent application No. 814,961, filed Dec. 24, 1991. Depending on the substrate requirements of this enzyme, it may be possible to discriminate between a fully matched RNA·DNA duplex and a duplex containing a single mismatch by employing oligonucleotides of this nature that place the RNaseH recognition site at the mismatch. If the enzyme is unable to bind or cleave a mismatch, additional selectivity will be obtained beyond that conferred by $\Delta\Delta G°_{37}$.

What is claimed is:

1. An antisense oligonucleotide comprising from 15 to 30 nucleotide units with a phosphodiester or phosphorothioate internucleoside linkage targeted to codon 12 of the human H-ras gene wherein said oligonucleotide is complementary and hybridizes to messenger RNA derived from the human H-ras gene so that the normal role of the messenger RNA is interfered with causing a loss of its function within a cell.

2. A method of modulating the expression of the human H-ras gene comprising contacting tissues or cells containing the gene with an antisense oligonucleotide comprising from 15 to 30 nucleotide units with a phosphodiester or phosphorothioate internucleoside linkage targeted to codon 12 of the human H-ras gene wherein said oligonucleotide is complementary and hybridizes to messenger RNA derived from the human H-ras gene so that the normal role of the messenger RNA is interfered with causing a loss of its function within a cell.

3. A method of detecting mutant H-ras based on the differential affinity of particular oligonucleotides for mutant vs. wild-type H-ras comprising contacting cells or tissues suspected of containing it with the oligonucleotide: 5' CCA-CAC-CGA-CGG-CGC-CC 3', SEQ ID NO: 3 and contacting an identical sample of cells or tissues with one of the oligonucleotides:

5' .......................3'

CTT ATA TTC CGT CAT CGC TC,   SEQ ID NO: 1;

TCC GTC ATC GCT CCT CAG GG,   SEQ ID NO: 2;

CCC ACA CCG ACG GCG CCC A,   SEQ ID NO: 4;

GCC CAC ACC GAC GGC GCC CAC,   SEQ ID NO: 5; or

TGC CCA CAC CGA CGG CGC CCA CC,   SEQ ID NO: 6.

4. An oligonucleotide having SEQ ID NO: 1, SEQ ID NO: 2, SEQ ID NO: 3, SEQ ID NO: 4, SEQ ID NO: 5, SEQ ID NO: 6, or SEQ ID NO: 15 with a phosphodiester or phosphorothioate internucleoside linkage.

5. The method of claim 2 wherein said oligonucleotide has SEQ ID NO: 3, SEQ ID NO: 4, SEQ ID NO: 5, SEQ ID NO: 6, or SEQ ID NO: 15 with a phosphodiester or phosphorothioate internucleoside linkage.

6. A method of modulating the expression of the human H-ras gene comprising contacting tissues or cells containing the gene with an antisense oligonucleotide comprising SEQ ID NO: 1 or SEQ ID NO: 2 having a phosphodiester or phosphorothioate internucleoside linkage.

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
        ( A ) LENGTH: 20
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 1:

CTTATATTCC GTCATCGCTC                                                            2 0

( 2 ) INFORMATION FOR SEQ ID NO: 2:

( i ) SEQUENCE CHARACTERISTICS:
        ( A ) LENGTH: 20
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 2:

TCCGTCATCG CTCCTCAGGG                                                            2 0

( 2 ) INFORMATION FOR SEQ ID NO: 3:

( i ) SEQUENCE CHARACTERISTICS:
        ( A ) LENGTH: 17
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 3:

CCACACCGAC GGCGCCC                                                               1 7

( 2 ) INFORMATION FOR SEQ ID NO: 4:

( i ) SEQUENCE CHARACTERISTICS:
        ( A ) LENGTH: 19
        ( B ) TYPE: nucleic acid
        ( C ) STRANDEDNESS: single stranded
        ( D ) TOPOLOGY: linear (iv) ANTI-SENSE: YES (xi) SEQUENCE DESCRIPTION: SEQ ID NO: 4:

CCCACACCGA CGGCGCCCA  19

(2) INFORMATION FOR SEQ ID NO: 5:

(i) SEQUENCE CHARACTERISTICS:
    (A) LENGTH: 21
    (B) TYPE: nucleic acid
    (C) STRANDEDNESS: single stranded
    (D) TOPOLOGY: linear (iv) ANTI-SENSE: YES (xi) SEQUENCE DESCRIPTION: SEQ ID NO: 5:

GCCCACACCG ACGGCGCCCA C  21

(2) INFORMATION FOR SEQ ID NO: 6:

(i) SEQUENCE CHARACTERISTICS:
    (A) LENGTH: 23
    (B) TYPE: nucleic acid
    (C) STRANDEDNESS: single stranded
    (D) TOPOLOGY: linear (iv) ANTI-SENSE: YES (xi) SEQUENCE DESCRIPTION: SEQ ID NO: 6:

TGCCCACACC GACGGCGCCC ACC  23

(2) INFORMATION FOR SEQ ID NO: 7:

(i) SEQUENCE CHARACTERISTICS:
    (A) LENGTH: 47
    (B) TYPE: nucleic acid
    (C) STRANDEDNESS: single stranded
    (D) TOPOLOGY: linear (iv) ANTI-SENSE: NO (xi) SEQUENCE DESCRIPTION: SEQ ID NO: 7:

ACATTATGCT AGCTTTTTGA GTAAACTTGT GGGGCAGGAG ACCCTGT  47

(2) INFORMATION FOR SEQ ID NO: 8:

(i) SEQUENCE CHARACTERISTICS:
    (A) LENGTH: 29
    (B) TYPE: nucleic acid
    (C) STRANDEDNESS: single stranded
    (D) TOPOLOGY: linear (iv) ANTI-SENSE: YES (xi) SEQUENCE DESCRIPTION: SEQ ID NO: 8:

GAGATCTGAA GCTTCTGGAT GGTCAGCGC  29

(2) INFORMATION FOR SEQ ID NO: 9:

(i) SEQUENCE CHARACTERISTICS:
    (A) LENGTH: 35
    (B) TYPE: nucleic acid
    (C) STRANDEDNESS: single stranded
    (D) TOPOLOGY: linear (iv) ANTI-SENSE: NO (xi) SEQUENCE DESCRIPTION: SEQ ID NO: 9:

GAGATCTGAA GCTTGAAGAC GCCAAAAACA TAAAG                                           35

( 2 ) INFORMATION FOR SEQ ID NO: 10:

( i ) SEQUENCE CHARACTERISTICS:
        ( A ) LENGTH: 33
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 10:

ACGCATCTGG CGCGCCGATA CCGTCGACCT CGA                                             33

( 2 ) INFORMATION FOR SEQ ID NO: 11:

( i ) SEQUENCE CHARACTERISTICS:
        ( A ) LENGTH: 20
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 11:

CTCGCTACTG CCTTATATTC                                                            20

( 2 ) INFORMATION FOR SEQ ID NO:12:

( i ) SEQUENCE CHARACTERISTICS:
        ( A ) LENGTH: 20
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 12:

GGGACTCCTC GCTACTGCCT                                                            20

( 2 ) INFORMATION FOR SEQ ID NO: 13:

( i ) SEQUENCE CHARACTERISTICS:
        ( A ) LENGTH: 11
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 13:

CACCGACGGC G                                                                     11

( 2 ) INFORMATION FOR SEQ ID NO: 14:

( i ) SEQUENCE CHARACTERISTICS:
        ( A ) LENGTH: 13
        ( B ) TYPE: nucleic acid
        ( C ) STRANDEDNESS: single stranded
        ( D ) TOPOLOGY: linear ( i v ) ANTI-SENSE: YES ( x i ) SEQUENCE DESCRIPTION: SEQ ID NO: 14:

ACACCGACGG CGC                                                                   13

( 2 ) INFORMATION FOR SEQ ID NO: 15:

(i) SEQUENCE CHARACTERISTICS:
  (A) LENGTH: 15
  (B) TYPE: nucleic acid
  (C) STRANDEDNESS: single stranded
  (D) TOPOLOGY: linear (iv) ANTI-SENSE: YES (xi) SEQUENCE DESCRIPTION: SEQ ID NO: 15:

CACACCGACG GCGCC 15

(2) INFORMATION FOR SEQ ID NO: 16:

(i) SEQUENCE CHARACTERISTICS:
    (A) LENGTH: 16
    (B) TYPE: nucleic acid
    (C) STRANDEDNESS: single stranded
    (D) TOPOLOGY: linear (iv) ANTI-SENSE: YES (xi) SEQUENCE DESCRIPTION: SEQ ID NO: 16:

CCACACCGAC GGCGCC 16

(2) INFORMATION FOR SEQ ID NO: 17:

(i) SEQUENCE CHARACTERISTICS:
    (A) LENGTH: 16
    (B) TYPE: nucleic acid
    (C) STRANDEDNESS: single stranded
    (D) TOPOLOGY: linear (iv) ANTI-SENSE: YES (xi) SEQUENCE DESCRIPTION: SEQ ID NO: 17:

CACACCGACG GCGCCC 16

(2) INFORMATION FOR SEQ ID NO: 18:

(i) SEQUENCE CHARACTERISTICS:
    (A) LENGTH: 18
    (B) TYPE: nucleic acid
    (C) STRANDEDNESS: single stranded
    (D) TOPOLOGY: linear (iv) ANTI-SENSE: YES (xi) SEQUENCE DESCRIPTION: SEQ ID NO: 18:

CCCACACCGA CGGCGCCC 18

(2) INFORMATION FOR SEQ ID NO: 19:

(i) SEQUENCE CHARACTERISTICS:
    (A) LENGTH: 18
    (B) TYPE: nucleic acid
    (C) STRANDEDNESS: single stranded
    (D) TOPOLOGY: linear (iv) ANTI-SENSE: YES (xi) SEQUENCE DESCRIPTION: SEQ ID NO: 19:

CCA CAC CGA CGG CGC CCA 18

(2) INFORMATION FOR SEQ ID NO: 20:

(i) SEQUENCE CHARACTERISTICS:
    (A) LENGTH: 19
    (B) TYPE: nucleic acid
    (C) STRANDEDNESS: single stranded
    (D) TOPOLOGY: linear (i v) ANTI-SENSE: YES (x i) SEQUENCE DESCRIPTION: SEQ ID NO: 20:

ACCCGCGGCA GCCACACCC 19

(2) INFORMATION FOR SEQ ID NO: 21:

(i) SEQUENCE CHARACTERISTICS:
        (A) LENGTH: 20
        (B) TYPE: nucleic acid
        (C) STRANDEDNESS: single stranded
        (D) TOPOLOGY: linear (i v) ANTI-SENSE: YES (x i) SEQUENCE DESCRIPTION: SEQ ID NO: 21:

CACCCGCGGA GCCACACCCG 20

(2) INFORMATION FOR SEQ ID NO: 22:

(i) SEQUENCE CHARACTERISTICS:
        (A) LENGTH: 23
        (B) TYPE: nucleic acid
        (C) STRANDEDNESS: single stranded
        (D) TOPOLOGY: linear (i v) ANTI-SENSE: YES (x i) SEQUENCE DESCRIPTION: SEQ ID NO: 22:

CCACCCGCGG CAGCCACACC CGT 23

(2) INFORMATION FOR SEQ ID NO: 23:

(i) SEQUENCE CHARACTERISTICS:
        (A) LENGTH: 25
        (B) TYPE: nucleic acid
        (C) STRANDEDNESS: single stranded
        (D) TOPOLOGY: linear (i v) ANTI-SENSE: YES (x i) SEQUENCE DESCRIPTION: SEQ ID NO: 23:

TTGCCCACAC CGACGGCGCC CACCA 25

(2) INFORMATION FOR SEQ ID NO: 24:

(i) SEQUENCE CHARACTERISTICS:
        (A) LENGTH: 72
        (B) TYPE: nucleic acid
        (C) STRANDEDNESS: single stranded
        (D) TOPOLOGY: linear (i v) ANTI-SENSE: YES (x i) SEQUENCE DESCRIPTION: SEQ ID NO: 24:

GGCCCCUGAG GAGCGAUGAC GGAAUAUAAG CUGGUGGUGG UGGGCGCCGU 50

CGGUGUGGGC AAGAGUGCGC UG 72